United States Patent [19]

Weir, Jr.

[11] 4,051,436
[45] Sept. 27, 1977

[54] APPARATUS FOR AND METHOD OF MEASURING POLARIZATION POTENTIAL OF A METALLIC STRUCTURE

[76] Inventor: Casper J. Weir, Jr., Rte. 3, Box 215-B, San Luis Obispo, Calif. 93401

[21] Appl. No.: 676,710

[22] Filed: Apr. 14, 1976

[51] Int. Cl.² .................. G01R 19/00; G01R 1/14
[52] U.S. Cl. .................. 324/102; 73/430; 204/195 C; 204/196; 324/125
[58] Field of Search .................. 324/102, 71 C, 157, 324/125, 29; 73/86, 430; 204/147, 196, 1 C, 195 C

[56] References Cited

U.S. PATENT DOCUMENTS

| | | | |
|---|---|---|---|
| 1,702,444 | 2/1929 | Kelly, Jr. | 73/430 |
| 3,327,214 | 6/1967 | Allen et al. | 324/29 |

*Primary Examiner*—Rudolph V. Rolinec
*Assistant Examiner*—Ernest F. Karlsen
*Attorney, Agent, or Firm*—Huebner & Worrel

[57] ABSTRACT

An improved testing device and method to measure the degree of polarization potential on the interface of a metal structure and its environment where said structure is protected against corrosion through a cathodic protection system.

The testing device includes adjustable stop means associated with a conventional electrometer to reduce the excursion of the needle of said meter and thereby achieve a more accurate reading of the polarization potential of the metal structure.

8 Claims, 4 Drawing Figures

APPARATUS FOR AND METHOD OF MEASURING POLARIZATION POTENTIAL OF A METALLIC STRUCTURE

BACKGROUND OF THE INVENTION

One of the big problems that confronts metallic objects in certain environments is the corrosion of these objects. Various rust preventatives have been developed over the years from combinations of metals to rust preventive paints and coatings.

However, one of the most effecive methods of corrosion protection is known as cathodic protection. Such a method is particularly applicable to metallic pipelines, underground metallic tanks, structures in contact with the earth, metallic ship hulls immersed in water, etc. Depending on polarity this method affords either cathodic or anodic protection. Anodic polarization is used in some specialized instances.

Cathodic protection may be achieved by making a metallic structure the cathode in an electrolytic cell. The anode in this cell may be of a metal more active, i.e. more positive in the electrochemical series, in which case, consumption of the anode furnishes the power required for the process. The more commonly used metals used in conjunction with steel or iron are, aluminum, magnesium, and zinc. Each of these metals has its particular adaptability to a situation. These anodes are often bonded, bolted or otherwise connected through a metallic circuit to the structure to be protected.

Other metals or substances less reactive such as iron, lead, and platinum may also be used as anode material. In this case, a power supply will be required to establish a flow of electricity in the system.

The current established in the electrical circuit from anode to the soil (electrolyte), soil to cathode, through the metallic path back to the anode will polarize the electrodes at the electrolyte interface. Polarization being the formation of an electromotive force (EMF) on the surface of the electrode in opposition to the established current. The degree of polarization is a measure of the level of protection of the subject structure or cathode.

With the development of the cathodic system of protection, it has also been desirable to be able to measure the polarization potential of the protected structure.

To accomplish this, suitable reference electrodes, or half-cells, are used with an electrometer, such as a conventional voltmeter or millivolt meter will be able to afford visual readings of the volt or millivolt polarization potential. Based upon a range of volts or millivolts required for the particular structure, readings can be taken and a determination made as to whether there is adequate cathodic protection of the metal structure.

There is, however, a difficulty with this mode of measurement because with a constant current the voltmeter in reality records the sum of two voltages, that sought and the other that is generated by the passage to the structure by the electric current in the environment between the reference cell and the structure.

One way in which efforts have been made to produce a true reading instead of a mixed reading is that of separating these two voltages by interrupting the current momentarily so that the potential may be observed when the current is off. This is usually done by cutting off the current for a preselected arbitrary time period which usually runs for 5 to 10 seconds, whereon at the conclusion of the period current is then turned on for a period of time, usually 25 seconds to 50 seconds. Such a schedule or "repeat cycle" is conveniently accomplished by an appropriate timer mechanism.

However, while it has been found that the "repeat cycle" technique is valuable for achieving a truer reading of the polarization potential of the metallic structure to be protected, other complications arise.

First the meter indicates a value which is the sum of the two voltages. Secondly, on interruption of the current, a new lesser value is instantaneously "felt at the meter," then while the current is "off" there is a rapid decay of the polarization potential which is reflected in movement of the needle of a voltmeter. It has been determined that such decay is a logarithmic function of several combined factors. Such factors include the degree of polarization at the particular time, the resistivity of the enviornment, and the effects of adjacent portions of the metallic structure being protected. The greater the degree of polarization, the faster the decay. The instantaneous change in voltage reflecting the electrical phenomena, at the instant of "off", cannot be read on a conventional voltmeter.

Most voltmeters of a sufficient sensitivity or accuracy cannot respond rapidly enough to indicate the fleeting or transient instantaneous "off" potential. Interpretation of data so obtained may result in assuming that at least some portions of a cathodic protection system is in jeopardy, when in fact this condition did not exist. In other words, it is impossible with present voltmeters to observe an instantaneous change from a high reading to a lower reading.

SUMMARY OF THE INVENTION

In order to compensate for the problems of rapid decay and interruption of current discussed above, the invention includes the use of a stop means which is adjustable and may be imposed in the path of a conventional needle or pointer of a voltmeter or millivolt meter.

An object of the invention is to, by use of the stop means, limit the upscale movement of the needle when the current is turned on to thus eliminate the time required for the downscale movement of excursion of the needle to the instantaneous "off" indication.

By the use of such a stop means needle excursion can be saved during the "repeat cycle", or on-off times, to achieve more nearly true indication of the instantaneous "off" polarization potential.

Further objects and advantages of the invention may be brought out in the following part of the specification wherein small details have been described for the competence of disclosure, without intending to limit the scope of the invention which is set forth in the appended claims.

BRIEF DESCRIPTION OF THE DRAWINGS

Referring to the accompanying drawing, which is for illustrative purposes.

DETAILED DESCRIPTION OF THE PREFERRED EMBODIMENT

Figure 1:
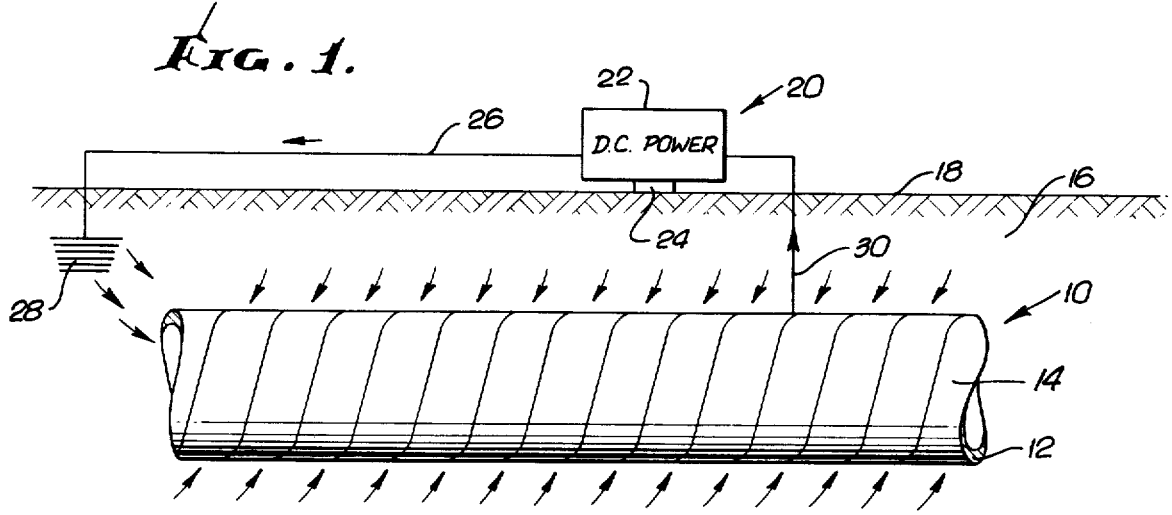
FIG. 1 illustrates a pipeline wherein the cathodic protection technique is being applied to inhibit corrosion of a pipeline.

There is illustrated in FIG. 1 the cathodic protection method of corrosion protection. For purposes of illustration, the method is being applied to a pipeline 10. The pipeline 10 is a conventional line including sections of pipe 12 welded or otherwise united to form the line 10. Generally, the sections 12 as they are secured together are then wrapped with a protective wrapping or coating 14 to impede deterioration of the pipe by corrosion or other means.

The pipeline 10 is set within the ground 16 and covered. Conventionally, pipelines are buried anywhere from a few feet to 20 feet or more below the ground surface 18.

In order to assure greater corrosion protection than just the protective wrapping 14, a cathodic protection system is utilized. In FIG. 1 there is illustrated a "drain station" or cathodic protection equipment 20. A D/C power source 22 (not shown in detail) is mounted on concrete pad or pole 24 and may be raised above the ground surface 18. The power source 22 is usually a generator, battery, rectifier or sacrificial anode. Further, the power source 22 can be mounted in an underground vault and work as effectively as being mounted above ground.

Depending on the newness of the pipeline 10, the electric current given off from the power source 22 can vary from a few milliampere on a new well coated line to as much as 150 amperes or more where pipelines are bare or have a deteriorated coating. The power source 22 serves to move electrical current through a wire 26 to an anode 28 buried in the ground 16. Anodes 28 may be made up of junk iron pieces, carbon, lead, platinum, etc.

To complete the drain station a wire 30 extends from the pipeline surface to the power source 22.

Thus in operation the power source 22 passes a current to the anode 28, and the current will then pass through the earth 16 which acts as an electrolytic medium to the pipeline 10, illustrated by arrows in FIG. 1, and then passes through the wire 30 to complete the electrolytic cell. With this cycle, the pipeline 10 becomes more negative to its environment and corrosion becomes inhibited in the pipeline 10 and increased in the sacrificial anode 28 thus extending the normal life of the line 10. Additionally, the electrical phenomena will occur whether the pipe is coated or not.

Because a pipeline 10 may be many miles in length, it may be necessary to place "drain stations" 20 at certain intervals along the pipeline.

During periods of surveillance the power surface 22 is fitted with repeat cycle interrupters (not shown) to turn the power source "on" for a specified period of time and then "off" for a predetermined period of time and then repeat the cycle. Generally, on pipelines the timing cycle varies from 30 seconds to one minute per cycle with "off" times of 5 to 10 seconds. The time intervals which are normaly used are entirely arbitrary and selected to suit the situation. The purpose of the time cycle will be subsequently explained.

The principle accomplished by the drain station 20 is to polarize the surface of the pipeline 10 by electrical current. That is a potential or voltage is generated on the surface in opposition to current entering the surface.

It has been found through use of the cathodic protection process that in pipelines a current force within specific ranges will accomplish the desired inhibition of corrosion. In order to determine if the proper amount of current is being supplied there are devices available to read the polarization potential.

In other words, by interpreting the potential measurements it can be determined whether the protection is adequate, inadequate or there is an excessive amount of current being supplied.

The same operation described above may also be used in a self-powered system where sacrificial anodes are used. In this case the repeat cycle timer is interposed in the metallic circuit. However, such positioning is impossible in a situation where the sacrificial anode is bonded to the structure surface, such as a galvanized object.

Generally speaking when an electrometer generally designated 32 is used with additional equipment to be explained, it is a conventional voltmeter or millivolt meter 34 having a dial 36 with increments in volts or millivolts as the case may be reading from 0 on the left to a number above the expected range on the right.

When such an electrometer 32 is used it has been found with an iron pipeline and environments that polarization potential should register within the range of between 850 millivolts and 2000 millivolts when an appropriate half-cell 42 is utilized. Thus if there is an incremental value on the dial 36 at the instantaneous "off" time more positive or downscale than 850 millivolts there is inadequate protection and the situation evaluated for possible correction. If on the other hand there is a registration of an incremental value on the dial 36 more negative or upscale than 2000 millivolts there is an indication of excessive use of electric current and it may be required to be adjusted downward. If the incremental value registration on the dial 36 is between 850 and 2000 millivolts adequate protection is assumed.

Figure 2:
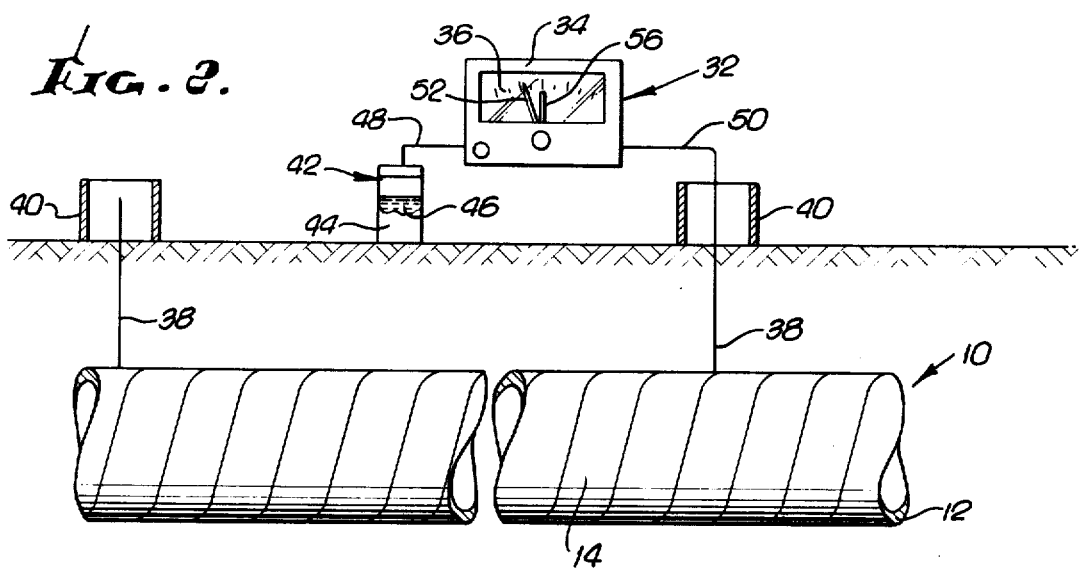
FIG. 2 illustrates test equipment used in connection with establishing the polarization potential of a pipeline at various intervals.

In order to make appropriate tests of the polarization potential of the pipeline 10, test wires 38 are bonded to the surface of the pipeline 10 at spaced distances one from the other (see FIG. 2). The test wires 38 are insulated and extend upwardly above the earth surface 16 and can have protectors 40 surrounding the wires 38 to prevent inadvertent dislodgment and as markers.

These test wires 38 in the case of a long pipeline 10 are arbitrarily spaced ½ mile to 1 mile apart, depending on need and accessibility.

In order to accomplish the necessary readings to determine adequate potential as discussed above, a reference electrode or half-cell 42 is necessary. There are many available conventional cells 42 such as the copper-copper sulphate electrode having a cylinder 44 containing the proper copper-copper sulphate solution 46 therein. A wire 48 is connected from the half-cell 42 to the conventional volt or millivolt meter 34. From the meter 34 there is a wire 50 which in turn is temporarily connected to a bared end of the test wire 38.

The voltmeter 34 in addition to the dial 36 includes a conventional registry needle 52 that will register on the dial 36 when the half-cell 42 is placed in contact with the soil or electrolytic medium 16 and the metallic circuit completed.

One of the difficulties with measuring the polarization potential of the surface of the pipeline 10 with a half-cell 42 and millivolt meter 34 is that if the current is constant at the drain station 20 the meter 34 will register the sum of two voltages, the polarization potential and the voltage created by passage of current through the electrolytic medium 16 between the half-cell 42 and line 10; both values are unknown.

In order to alleviate the problem the repeat cycle interrupter (discussed above) at the drain station 20 is used so that the two voltages, i.e. that sought and that generated by the passage of current through the environment, may be separated. In other words, by cycling the current for a predetermined time "on" and a predetermined time "off" the polarization potential of the metallic surface can be read during the "off" time.

However, the interruption of the current at the drain station 20 introduces two other problems. First when the current is turned "off" there is an instantaneous change in voltage "felt" by the meter 34 to the polarization potential. Then there is a very rapid decay of the polarization potential of the surface which is reflected in the movement of the needle 52 of the millivolt meter 34. Secondly, when the "on" time of the current is not of a sufficient duration equilibrium of current is not adequately restored particularly if the "off" time of the current is relatively long. This latter difficulty is particularly acute where the test wire 38 is remote from a drain station 20.

With the first problem enunciated above the instantaneous change of voltage makes it difficult to observe the real instantaneous "off" on the dial 36. The instantaneous "off" reading is necessary to observe the polarization potential that may be desired for proper evaluation of the level of protection of the system.

It has been found that with conventional meters 34 the instantaneous point in the "off" time cannot be truly read due to needle excursion and thus a lower level of protection will be indicated.

Regarding the second problem of maintaining a sufficient restoration of current, particularly at the test wires 38 remote the drain station 20, a measurement made under these circumstances might also indicate an unsatisfactory condition. This is due to the meter response time and also because the metallic surface might not have had time to fully recover its potential in view of a relatively long "off" time caused by the distance from the drain station 20.

In order to compensate for these problems an electrometer 32 has been modified with the subject of this invention.

Figure 3:
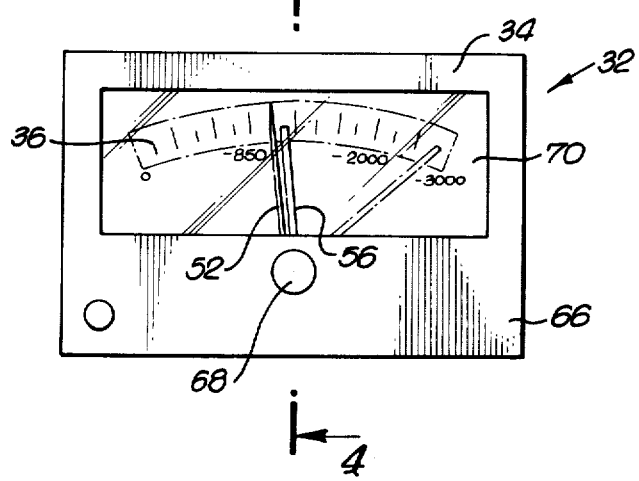
FIG. 3 is an enlarged view of the face and needle of an electrometer with the stop means of this invention in place.
Figure 4:
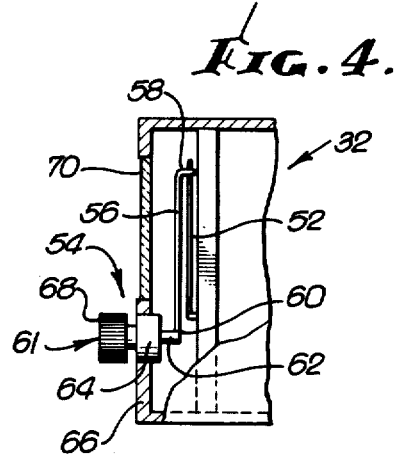
FIG. 4 is a side elevational cross-sectional view of the electrometer, taken on line 4—4 of FIG. 3.

As seen particularly in FIGS. 3 and 4 of the drawings a stop means 54 has been interposed in the millivolt meter 34. The stop means 54 includes an elongated relatively thin blade or wire 56 positioned over the conventional dial 36 and is spaced outwardly of the plane of rotational arc of the needle 52. The blade 56 includes a projection or end 58 bent normal to the length of the blade into the path of the needle 52 and will act as a stop to engage the needle 52.

The bottom end 60 of the blade 56 is attached to or formed with an adjustment means 61 including a rotatable shaft 62. The shaft 62 projects outwardly through a bearing 64 mounted in the front wall 66 of the electrometer 32 and terminated in an exterior knob 68.

Thus by rotating the knob 68 the blade 56 can be rotated and adjusted to act as a stop for the needle 52 during testing operations to overcome the problems of obtaining proper readings of metallic surface polarization potential during testings.

As an illustration, assuming the dial 36 registers millivolt increments starting at the left with 0 and going to 3000, the range between 850 millivolts shown on the left of the dial and 2000 millivolts shown on the right side is in effect the safe range or will show that there may be adequate protection of the metallic surface.

However, when the repeat cycle, as discussed above, is of an arbitrary cycle such as 30 seconds it means that the power at the drain station 20 is "on" for 25 seconds and "off" for 5 seconds, at which time it repeats again. Such a 5 second "off" time makes it impossible to achieve a proper reading unless the stop means 54 is utilized. With this means, a very brief "off" period is proposed as for example 1/10 or 1/5 second with a cycle time of 10 seconds.

In operation the half-cell 42 and electrometer 32 are hooked to the test wire as shown in FIG. 2 and the stop 56 is backed off to the right, such as shown by ghost lines in FIG. 3. The dial 36 is viewed by the tester for several cycles to make sure that everything is working properly. A cycle as registered on the electrometer 32 or millivolt meter 34 will show during "on" time the needle 52 moving up the scale to a particular point depending upon the polarization potential plus the I.R. loss through the earth 16 and then when the "on" time has elapsed and the current is turned "off" at the drain station 20, the needle 52 will move down scale or to the left toward a lower decreasing value point within the 5 second interval and at the conclusion of the 5 seconds when the power is again turned "on" at the drain station 20 the needle 52 will swing up scale to the right to the point previously registered. This "on" time excursion of the needle 52 is unnecessary and prevents a true reading.

As heretofore described, it is the instantaneous "off" condition of the drain station 20 where there is no exterior current that actually allows polarization potential of the surface of the pipeline 10 to be determined and evaluated. Because of inertia inherent in a coventional meter, appreciable time is required for the needle to arrive at the instantaneous "off" value or the greatest polarization potential. This potential, because of interruption of charging current, is also decreasing. In other words, if the needle is left free it will indicate, upscale, the sum of two voltages during the "on" portion of the cycle. Thus at the start of the "off" portion it will swing downscale toward the instantaneous "off" value. Because of the time required for excursion between these two values the true instantaneous "off" value has escaped and a lower value will be indicated. This lower point will be that which the physical limitations of the meter permit it to indicate the voltage at that time within the "off" period.

With the stop means 54 of this invention and the blade 56 backed off, that is to the right, of the needle 52, see FIG. 3, the operator can view the movement of the needle from left to right in the "on" stage and again to the left in the "off" stage so that each time the cycle is repeated the knob 68 can be rotated in turn moving the blade 56 downscale or to the left to a point where the upper end 58 can engage the needle 52 and prevent it from moving to the right or up the scale when the current is "on". In other words, it is unncessary to actually read the needle position when the current is "on" because the potential is only found when the current is off.

The optimum is to adjust the blade 56 of the stop means 54 to a downscale position which is really the fixed value point, hopefully no lower than 850 millivolts or higher than 2000 millivolts on the scale in the case of iron pipelines, so that the needle 52 just does not bounce downscale from the stop 54, but a bounce is impending.

In other words, with a proper adjustment of the stop 54 where the end 58 engages the needle 52, the needle will actually remain almost permanently fixed even though there is the aforementioned cycling of current.

As stated before the purpose of the stop 56 is to prevent unnecessary excursion of the needle 52 which because of the manual movement of the needle 52, cannot adjust itself to move appropriately within the interval of "off" times such as 5 to 10 seconds. Further it is very difficult to visually observe the fixed value point on the down side of the scale in a 5 second duration. However, with the stop means 54 and blade 56 properly adjusted so that the needle 52 merely bears against the stop and does not bounce because of the cycle "on" and "off", visually the reading can be seen and the intended result accomplished.

By eliminating the excursion time of the needle 52, a very brief "off" interval may be used on the order of 1/10 to 1/5 second. Thus the polarization potential decay will be reduced, and a more true indication will be observed. This reduced timing places less burden on the system because of deprivation of charging current.

Once the stop 54 is properly adjusted at one of the test wires 38, the setting is left at that adjusted position and the test apparatus is moved to the next test wire 38 further down the pipeline 10 for a reading. The same procedure can be repeated along the entire pipeline 10 at other test locations and the results evaluated after the surveillance is completed.

While the operation of the needle 52 and stop 54 have been illustrated where the values move from 0 on the left to 3000 on the right, if a different type of reference cell other than copper-copper sulphate 46 is used for the half-cell 42 as the reference electrode, such as a permanently installed magnesium anode, the needle 52 may be depressed toward or beyond the meter 0. Thus the needle 52 would move toward the left and accordingly it would be necessary to move the upper end 58 of the blade 56 from the side as shown in FIGS. 3 and 4 to the left side of the needle 52. To accomplish this a magnet could be used to draw blade 56 toward the glass 70 so that the needle 52 can clear the end 58 and move to the right side. With this arrangement the needle 52 will tend to bounce upscale, but the result is essentially the same as described when an anode half-cell 42 of copper-copper sulphate 46 is used.

While this invention has been illustrated as it would be used with regard to pipelines it should be realized that any metallic surface can be so protected such as the metal hull of a ship, a storage tank which is in contact with the earth that acts as the electrolytic medium, the interior of a tank, etc.

Although I have herein shown and described my invention in what I have conceived to be the most practical and preferred embodiment, it is recognized that departures may be made therefrom within the scope of my invention.

I claim:

1. An improved portable testing system for measuring the polarization potential of a metallic structure to determine if existing proper electrical current is presently being applied to said metallic structure to assure adequate cathodic protection of said metallic structure, wherein said cathodic protection is independently accomplished through at least one drain station in which the metallic structure is in contact with an electrolytic environment, a metallic lead from said metallic structure to an external normally energized power source, a metallic lead from said power source to an anode within said electrolytic environment, and a current interrupter is associated with said external normally energized electrical power source which can be activated to turn said power source off for a predetermined momentary period of time for testing said polarization potential and then on again, in which said portable testing system includes:

at least one metallic test lead projecting from said metallic structure through said electrolytic environment for external access away from said drain station;

an electrode half-cell adapted to contact said electrolytic environment adjacent said metallic test lead;

an electrometer connected to said electrode half-cell and having a terminal adapted to detachably receive said metallic test lead, said electrometer having a dial incrementally marked and a needle overlying said dial and adapted for movement back and fourth across said dial when said meter is connected to said metallic test lead, an adjustable stop means associated with said needle to prevent excursion of said needle across said dial in one direction to an incremental value when said power source is on, yet maintain said needle at an optimum incremental polarization potential value to acheive more nearly true indication of an instantaneous off when said power is momentarily off to visually determine if said needle remains relatively fixed which in turn indicates existing current is adequate.

2. An improved portable testing system as defined in claim 1 wherein the metallic structure extends for a distance and there are a plurality of metallic test leads spaced along said metallic structure, and said electrometer may be successively connected to each said leads to obtain an incremental polarization potential value along said metallic structure.

3. An improved portable testing system as defined in claim 1 wherein the metallic structure is an iron pipeline, and said electrolytic environment is earth, and there are a plurality of drain stations spaced therealong with a plurality of metallic test leads spaced between said drain stations, and said electrometer with a pre-setting of said stop means is successively connected to each of said leads to obtain an incremental polarization potential value along said pipeline to determine if said needle remains fixed and said existing current is adequate at the nearest drain station to said metallic test lead.

4. An improved portable testing system as defined in claim 3 wherein said electrometer is a millivolt meter and said pre-setting of said stop means is between 850 and 2000 millivolts, and said current off time is between ¼ of a second and 1 second.

5. An improved portable testing system as defined in claim 3, wherein said adjustable stop means is interposed within the path of said needle to physically block movement of said needle.

6. A method of measuring the polarization potential of a metallic structure to determine if existing proper electrical current is presently being applied to said metallic structure to assure adequate cathodic protection of said metallic structure, wherein a drain station is provided to render said cathodic protection in which said metallic structure is in contact with an electrolytic environment, a metallic lead is provided from said metallic structure to an external normally energized power source, a metallic lead is provided from said power source to an anode within said electrolytic environment, a current interrupter is associated with said external normally energized electrical power source which can be activated to turn said power source off for a predetermined momentary period of time for testing said polarization potential and then on again, including the steps of:

attaching metallic test leads away from said drain station to said metallic structure and projecting the same through said electrolytic environment for external access;

selecting a portable polarization potential testing device which includes an electronic half-cell, an electrometer connected to said electrode half-cell, said electrometer having a terminal adapted to detachably receive said metallic test lead, said electrometer having a dial incrementally marked and a needle overlying said dial, and adjustable stop means in the path of said needle;

placing said electrode half-cell adjacent one of said metallic test leads, and connecting said terminal of said electrometer to said metallic test lead;

activating said current interrupter whereby said electrical current is momentarily turned off, at which precise moment true polarization potential may be measured and then energizing said power source and repeating the cycle;

rotating said adjustable stop means to a position juxtaposed with said needle when said needle reaches an optimum value on said dial when said power source is momentarily off during one of said cycles, whereby said needle will be prevented from moving to a higher value when said power is on and unnecessary needle excursion is prevented during further repeat on-off cycles; and visually determining if said needle remains relatively fixed during said off time which in turn will indicate said existing current is adequate to assure cathodic protection.

7. A method as defined in claim 6 wherein the step of selecting a portable polarization potential testing device includes selecting a millivolt meter as the electrometer and the dial is incrementally marked in millivolts.

8. A method as defined in claim 7 wherein the metallic structure is an iron pipeline and the electrolytic environment is the earth, and the adjustable stop means in the millivolt meter is rotated to a value between 850 and 2000 millivolts.

* * * * *